US009131932B2

(12) United States Patent
Tegels (10) Patent No.: US 9,131,932 B2
(45) Date of Patent: Sep. 15, 2015

(54) DUAL LUMEN CARRIER TUBE WITH RETRACTABLE SLEEVE AND METHODS

(71) Applicant: St. Jude Medical Puerto Rico LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 383 days.

(21) Appl. No.: 13/757,238

(22) Filed: Feb. 1, 2013

(65) Prior Publication Data

US 2014/0222064 A1 Aug. 7, 2014

(51) Int. Cl.
| A61B 17/08 | (2006.01) |
| A61D 1/00 | (2006.01) |
| A61B 17/00 | (2006.01) |
| A61B 17/04 | (2006.01) |

(52) U.S. Cl.
CPC ... *A61B 17/0057* (2013.01); *A61B 2017/00663* (2013.01); *A61B 2017/00672* (2013.01); *A61B 2017/0417* (2013.01); *A61B 2017/0496* (2013.01)

(58) Field of Classification Search
CPC .................. A61B 17/0057; A61B 2017/00663; A61B 2017/0496; A61B 2017/0417; A61B 2017/00672
USPC ......... 606/213, 232; 604/168.01, 900, 30–34, 604/6.1
See application file for complete search history.

(56) References Cited

U.S. PATENT DOCUMENTS

| 5,222,974 | A | * | 6/1993 | Kensey et al. | 606/213 |
| 5,282,827 | A | * | 2/1994 | Kensey et al. | 606/215 |
| 5,306,254 | A | * | 4/1994 | Nash et al. | 604/168.01 |
| 5,411,520 | A | * | 5/1995 | Nash et al. | 606/213 |
| 5,507,744 | A | * | 4/1996 | Tay et al. | 606/50 |
| 5,531,759 | A | * | 7/1996 | Kensey et al. | 606/213 |
| 5,545,178 | A | * | 8/1996 | Kensey et al. | 606/213 |
| 5,649,959 | A | * | 7/1997 | Hannam et al. | 606/213 |
| 5,676,689 | A | * | 10/1997 | Kensey et al. | 606/213 |
| 5,728,132 | A | * | 3/1998 | Van Tassel et al. | 606/213 |
| 5,800,408 | A | * | 9/1998 | Strauss et al. | 604/264 |
| 5,810,884 | A | * | 9/1998 | Kim | 606/213 |
| 5,843,022 | A | * | 12/1998 | Willard et al. | 604/30 |
| 6,033,401 | A | * | 3/2000 | Edwards et al. | 606/41 |
| 6,063,085 | A | * | 5/2000 | Tay et al. | 606/50 |
| 6,193,670 | B1 | * | 2/2001 | Van Tassel et al. | 600/486 |
| 6,302,898 | B1 | * | 10/2001 | Edwards et al. | 606/214 |
| 6,425,911 | B1 | * | 7/2002 | Akerfeldt et al. | 606/213 |
| 6,488,662 | B2 | * | 12/2002 | Sirimanne | 604/164.01 |
| 6,500,152 | B1 | * | 12/2002 | Illi | 604/164.07 |
| 7,577,477 | B2 | * | 8/2009 | Allen et al. | 604/21 |
| 8,382,793 | B2 | * | 2/2013 | Egnelov et al. | 606/213 |
| 8,382,795 | B2 | * | 2/2013 | Forsberg et al. | 606/213 |
| 8,590,760 | B2 | * | 11/2013 | Cummins et al. | 227/175.1 |
| 8,641,675 | B2 | * | 2/2014 | Stout et al. | 604/167.02 |

(Continued)

*Primary Examiner* — Amy R Weisberg
(74) *Attorney, Agent, or Firm* — Holland & Hart (57) ABSTRACT

A vascular closure device includes a carrier tube and a sleeve. The carrier tube includes at least first and second lumens, the first lumen being configured to hold a sealing member, the second lumen being configured to provide blood flow from a distal opening thereof to a proximal opening thereof. The sleeve is positioned on the carrier tube and movable from a first position wherein blood flow through the second lumen is unobstructed, and a second position covering the distal and proximal openings to block blood flow through the second lumen.

17 Claims, 12 Drawing Sheets

(56) References Cited

U.S. PATENT DOCUMENTS

| | | | |
|---|---|---|---|
| 8,672,888 B2* | 3/2014 | Tal | 604/164.01 |
| 2004/0143290 A1* | 7/2004 | Brightbill | 606/213 |
| 2004/0158287 A1* | 8/2004 | Cragg et al. | 606/213 |
| 2005/0085773 A1* | 4/2005 | Forsberg | 604/164.01 |
| 2005/0085851 A1* | 4/2005 | Fiehler et al. | 606/213 |
| 2005/0096697 A1* | 5/2005 | Forsberg et al. | 606/213 |
| 2005/0125030 A1* | 6/2005 | Forsberg et al. | 606/213 |
| 2005/0125031 A1* | 6/2005 | Pipenhagen et al. | 606/213 |
| 2005/0283187 A1* | 12/2005 | Longson | 606/213 |
| 2006/0155330 A1* | 7/2006 | Michlitsch | 606/232 |
| 2006/0229672 A1* | 10/2006 | Forsberg | 606/232 |
| 2006/0229673 A1* | 10/2006 | Forsberg | 606/232 |
| 2006/0229674 A1* | 10/2006 | Forsberg | 606/232 |
| 2006/0265006 A1* | 11/2006 | White et al. | 606/232 |
| 2006/0276838 A1* | 12/2006 | Wensel et al. | 606/213 |
| 2007/0032823 A1* | 2/2007 | Tegg | 606/232 |
| 2007/0032824 A1* | 2/2007 | Terwey | 606/232 |
| 2007/0255314 A1* | 11/2007 | Forsberg | 606/213 |
| 2008/0071311 A1* | 3/2008 | White et al. | 606/232 |
| 2008/0215087 A1* | 9/2008 | Pavcnik et al. | 606/213 |
| 2008/0287986 A1* | 11/2008 | Thor et al. | 606/213 |
| 2009/0171282 A1* | 7/2009 | Pipenhagen et al. | 604/103.01 |
| 2010/0168791 A1* | 7/2010 | Kassab et al. | 606/213 |
| 2010/0185140 A1* | 7/2010 | Kassab et al. | 604/28 |
| 2010/0185234 A1* | 7/2010 | Fortson et al. | 606/213 |
| 2010/0191279 A1* | 7/2010 | Kassab et al. | 606/213 |
| 2010/0217308 A1* | 8/2010 | Hansen | 606/213 |
| 2010/0217312 A1* | 8/2010 | Hill et al. | 606/213 |
| 2010/0286727 A1* | 11/2010 | Terwey | 606/213 |
| 2011/0066181 A1* | 3/2011 | Jenson et al. | 606/213 |
| 2011/0224720 A1* | 9/2011 | Kassab et al. | 606/213 |
| 2012/0010634 A1* | 1/2012 | Crabb et al. | 606/144 |
| 2012/0089177 A1* | 4/2012 | Tegels | 606/213 |
| 2012/0101525 A1* | 4/2012 | Jenson et al. | 606/232 |
| 2012/0143245 A1* | 6/2012 | Tegels | 606/213 |
| 2012/0157913 A1* | 6/2012 | Aziz et al. | 604/28 |
| 2012/0158044 A1* | 6/2012 | Jenson et al. | 606/213 |
| 2012/0158045 A1* | 6/2012 | Pipenhagen | 606/213 |
| 2012/0165854 A1* | 6/2012 | Pipenhagen et al. | 606/191 |
| 2012/0245597 A1* | 9/2012 | Tegels | 606/138 |
| 2013/0006297 A1* | 1/2013 | Drasler | 606/213 |
| 2013/0060279 A1* | 3/2013 | Yassinzadeh | 606/213 |
| 2013/0103077 A1* | 4/2013 | Ditter | 606/213 |
| 2013/0138149 A1* | 5/2013 | Tegels | 606/232 |
| 2013/0178895 A1* | 7/2013 | Walters et al. | 606/213 |
| 2013/0226227 A1* | 8/2013 | Terwey | 606/213 |
| 2013/0253579 A1* | 9/2013 | Hundertmark et al. | 606/214 |
| 2014/0039547 A1* | 2/2014 | White | 606/213 |
| 2014/0046217 A1* | 2/2014 | Lim | 600/585 |
| 2014/0052171 A1* | 2/2014 | Tegels | 606/213 |
| 2014/0058438 A1* | 2/2014 | Terwey et al. | 606/213 |
| 2014/0135825 A1* | 5/2014 | Tegels et al. | 606/213 |
| 2014/0135826 A1* | 5/2014 | Tegels et al. | 606/213 |
| 2014/0142618 A1* | 5/2014 | Leopold et al. | 606/213 |
| 2014/0172012 A1* | 6/2014 | Stanley et al. | 606/213 |
| 2014/0180332 A1* | 6/2014 | Walters et al. | 606/213 |
| 2014/0188160 A1* | 7/2014 | Tegels | 606/213 |
| 2014/0200611 A1* | 7/2014 | Walters | 606/213 |
| 2014/0222063 A1* | 8/2014 | Terwey | 606/213 |
| 2014/0222064 A1* | 8/2014 | Tegels | 606/213 |
| 2014/0257372 A1* | 9/2014 | Tegels et al. | 606/213 |
| 2014/0277111 A1* | 9/2014 | Tegels | 606/213 |
| 2015/0018871 A1* | 1/2015 | Phillips et al. | 606/213 |

\* cited by examiner

DUAL LUMEN CARRIER TUBE WITH RETRACTABLE SLEEVE AND METHODS

TECHNICAL FIELD

The present disclosure relates generally to medical devices, and more particularly to vascular closure devices.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

Prior closure devices place an anchor inside the vessel to provide a backstop against which a sealing member that is positioned outside the vessel may be compressed. In some instances, a particular shaped insertion sheath is used to help position the anchor within the vessel and limit shuttling (return movement) of the anchor back into the insertion sheath. This insertion sheath may be structured differently from the insertion sheath that is used for procedures related to treating the patient prior to sealing the vessel puncture with the vascular closure device. Requiring a sheath exchange as part of sealing the vessel puncture has many disadvantages.

SUMMARY

One aspect of the present disclosure relates to a vascular closure device that includes a carrier tube and a sleeve. The carrier tube includes at least first and second lumens, the first lumen being configured to hold a sealing member, the second lumen being configured to provide blood flow from a distal opening thereof to a proximal opening thereof. The sleeve is positioned on the carrier tube and movable from a first position wherein blood flow through the second lumen is unobstructed, and a second position covering the distal and proximal openings to block blood flow through the second lumen.

The vascular closure device may include an anchor positionable between an outer surface of the carrier tube and an inner surface of the sleeve when the sleeve is in the first position, and moving the sleeve from the first position to the second position releases the anchor to rotate relative to the carrier tube. The second lumen may include inlet and outlet openings formed in a sidewall of the carrier tube. The sleeve may include at least first and second openings formed in a sidewall thereof, and the inlet and outlet openings of the sleeve are aligned with the inlet and outlet openings of the second lumen when the sleeve is in the first position. The second lumen may terminate at a location along the carrier tube proximal of the first lumen.

The sleeve may move axially between the first and second positions. The first lumen may include a distal portion and a proximal portion, wherein the distal portion has a greater cross-sectional size than the proximal portion. The vascular closure device may include a handle assembly connected to a proximal end of the carrier tube and a proximal end of the sleeve, wherein the handle assembly includes an actuator operable to move the sleeve relative to the carrier tube. The second lumen may have a non-circular cross sectional shape. A distal end portion of the carrier tube may be elastically deformable to define a recess along an outer surface thereof, and a portion of the anchor is positioned in the recess.

Another aspect of the present disclosure relates to a vascular closure system that includes an insertion sheath and a vascular closure device having a carrier tube, an anchor, and a sealing plug. The insertion sheath has a distal end and is configured for insertion through a vessel puncture. The carrier tube of the vascular closure device includes first and second lumens and is positionable within the insertion sheath. The anchor is positioned at a distal end of the carrier tube. The sealing plug is positioned in the first lumen of the carrier tube and coupled to the anchor with a suture that extends through the first lumen. The second lumen includes inlet and outlet ports configured to provide blood flow into and out of the second lumen.

The inlet and outlet ports may be formed in a sidewall of the carrier tube. The vascular closure system may include a sleeve positionable over the carrier tube, wherein the sleeve is movable relative to the carrier tube from a first position holding the anchor in a stored position and permitting blood flow through the second lumen, to a second position wherein the anchor is in a released position and blood flow through the second lumen is blocked. The sleeve may include at least a first port formed in a sidewall thereof that aligns with the outlet port of the carrier tube when the sleeve is in the first position. The first lumen may have at least one of a variable cross-sectional shape and a variable cross-sectional size along a length thereof. The second lumen may terminate at a location spaced proximal of a distal end of the carrier tube. The sleeve may be movable from the second position to the first position to move the anchor from the released position to the stored position.

A further aspect of the present disclosure relates to a method of operating a vascular closure device. The method includes providing a carrier tube having first and second lumens, a sleeve positionable over the carrier tube, an anchor positioned at a distal end of the carrier tube, and a sealing plug positioned in the first lumen of the carrier tube and coupled to the anchor with a suture that extends through the first lumen. The method further includes moving the sleeve relative to the carrier tube from a first position holding the anchor in a stored position and permitting blood flow through the second lumen, to a second position wherein the anchor is in a released position and blood flow through the second lumen is blocked.

The carrier tube may include at least one distal port formed in a sidewall thereof, wherein the sleeve provides access to the at least one distal port when in the first position and covers the at least one distal port in the second position. The sleeve may include at least one opening formed in a sidewall thereof that aligns with the at least one distal port when the sleeve is in the first position. The anchor may be positioned between an outer surface of the carrier tube and an inner surface of the sleeve when in the stored position, wherein the anchor is pivotable relative to the carrier tube when in the released position.

Another example method in accordance with the present disclosure is directed to a method of treating a puncture in a vessel. The method includes providing an insertion sheath and a vascular closure device, the vascular closure device comprising a carrier tube having at least first and second lumens, a sleeve positionable over the carrier tube, an anchor positioned at a distal end of the carrier tube, and a sealing plug positioned in the first lumen of the carrier tube and coupled to the anchor with a suture that extends through the first lumen. The method further includes inserting the insertion sheath into the puncture, arranging the sleeve relative to the carrier tube in a first position in which the anchor is held in a stored position and a fluid path through the second lumen is open, inserting the vascular closure device through the insertion sheath until blood flows through the second lumen, moving the sleeve from the first position into a second position to release the anchor and close the fluid path, and withdrawing the vascular closure device to draw the anchor into contact with an inner surface of the vessel adjacent to the puncture and to deposit the sealing plug adjacent to the puncture exterior of the vessel to seal the puncture.

The vascular closure device may further include a compaction member, and the method includes operating the compaction member to compact the sealing plug toward the anchor. The carrier tube may include a distal port formed in a sidewall thereof providing access to the second lumen, and the carrier tube covers the distal port when in the second position. Moving the sleeve may include retracting the sleeve in a proximal direction.

Additional advantages and novel features will be set forth in the description which follows or can be learned by those skilled in the art through reading these materials or practicing the examples disclosed herein. The advantages of the invention can be achieved through the means recited in the attached claims.

BRIEF DESCRIPTION OF THE DRAWINGS

The accompanying drawings illustrate various embodiments of the present disclosure and are a part of the specification. The illustrated embodiments are merely examples and do not limit the scope of the present disclosure.

DETAILED DESCRIPTION

As mentioned above, vascular procedures are conducted throughout the world and require access to a vessel through a puncture. Often, the vessel is a femoral artery. To close the puncture following completion of the procedure, many times a closure device is used to sandwich the puncture between an anchor and a sealing plug. A suture may be used to couple together the anchor and sealing plug. A force may be applied along the suture to draw the anchor and sealing plug toward each other as the sealing plug is compressed against the puncture. Typically, the suture is manually cut at a location outside of the patient after confirmation that the puncture has been sealed.

The anchor is usually intended to remain in the vessel (intraluminal) at least while the puncture in the vessel is sealed. Some insertion sheaths used with such vascular closure devices include a monofold structure at a distal end of the insertion sheath. The monofold structure provides an obstruction to return passage of the anchor member into the insertion sheath after the anchor has been deployed distally from the insertion sheath. The distal end of the insertion sheath, due in part to the monofold structure, may provide a surface against which the anchor engages to rotate the anchor into a position generally parallel with the internal wall of the vessel. The anchor may then abut against the vessel wall when the insertion sheath is retracted from the puncture.

A sheath exchange after treatment of the patient and prior to using the vascular closure device is typically required due to the differences between procedural insertion sheaths that are used with patient treatment instruments and closure insertion sheaths with monofold structures that are used with vascular closure devices. Sheath exchanges have several potential disadvantages and are avoided if possible. A sheath exchange typically requires two different sheaths, one being exchanged for the other, which results in higher equipment costs, greater complexity in the procedure, and increased time requirement for completion of the procedure. A sheath exchange may also result in increased risk of damaging the patient or introducing infection at the treatment site.

The present disclosure is directed to a vascular closure device that includes a carrier tube with features that effectively eliminate the need for exchanging a procedure insertion sheath to a sheath designed specifically for use with a vascular closure device. Alternatively, the vascular closure device of the present disclosure may be used with an insertion sheath designed specifically for use with the vascular closure device and that potentially eliminates the need for a sheath exchange. Sheaths typically used with vascular closure devices include blood flashback capabilities that assist in confirming insertion depth for the vascular closure device.

The carrier tube may include a deformable distal portion that provides nesting of the anchor along an outer surface of the carrier tube and within the insertion sheath prior to deployment of the anchor. The distal portion of the carrier tube may recoil from the deformed position to an undeformed position after deployment of the anchor. The carrier tubes of the present disclosure permit the same insertion sheath that is used for treatment of the patient to be used with a vascular closure device that utilizes an intraluminal anchor to seal the vessel puncture.

One aspect of the present disclosure is directed to a vascular closure device having a carrier tube through which a sealing plug is delivered to a vessel puncture for sealing the vessel puncture. The vascular closure device also includes an anchor that is positioned within the vessel interior. The vascular closure device may be referred to as an intravascular closure device, wherein the anchor is deposited within the vessel and tied to the sealing plug to help maintain the sealing plug in position relative to the vessel puncture.

The carrier tube may include at least two lumens, wherein one of the lumens is used for delivery of the sealing plug to the vessel puncture and the other lumen is used as a blood flashback lumen to assist in positioning the anchor within the vessel.

Another aspect of the present disclosure relates to a sleeve positioned over at least a portion of the carrier tube. The sleeve may control access to at least one of an inlet opening and an outlet opening for the flashback lumen of the carrier tube. In one example, the sleeve provides access to the inlet and outlet openings of the flashback lumen of the carrier tube when locating the vessel interior prior to depositing the anchor. The sleeve may be operable into a closed position in which access to at least the inlet to the flashback lumen is closed to stop blood flow through the flashback lumen after the vessel interior has been located.

The sleeve may also provide an anchor retaining function wherein the sleeve retains the anchor in a stowed position prior to locating the vessel interior using the flashback lumen. Operating the sleeve into another position such as a position closing access to the inlet of the flashback lumen may concurrently release the anchor within the vessel.

The sleeve may be operated at a proximal location using, for example, a trigger or actuating device that is positioned at a handle portion of the vascular closure device. The handle portion may be positioned at a proximal end of the carrier tube. The actuator may move the sleeve between distal and proximal positions to control access to the inlet and outlet openings of the flashback lumen. The actuator may actuate the sleeve between a position holding the anchor in the stowed position and a position in which the anchor is released from the stowed position.

The sleeve may also include secondary inlet and outlet openings at spaced apart locations along a length of the sleeve. The secondary inlet and outlet openings may align with the inlet and outlet openings of the flashback lumen when the sleeve is in a first or open position that provides access to the inlet and outlet openings of the flashback lumen. Operating the sleeve into a second or closed position moves the secondary inlet and outlet openings out of alignment with the inlet and outlet openings of the flashback lumen thereby stopping blood flow through the flashback lumen.

Referring now to FIGS. 1A-6, an example vascular closure device 10 is shown including a carrier tube 12, a sleeve 14, an anchor 16, a sealing plug 18, a compaction tube 20, a handle 22, and an actuator 24. A suture 26 may extend distally through the carrier tube 12 to connect to an eye 58 of the anchor 16.

The carrier tube 12 includes distal and proximal ends 30, 32, a first lumen 34, and a second lumen 36. The first and second lumens 34, 36 may be arranged in a parallel, side-by-side arrangement. Typically, the first lumen 34 has a larger cross-sectional area than the second lumen 36 (e.g., see FIG. 1B). The first lumen 34 may be used to deliver the sealing plug 18. The suture 26 may extend through the first lumen 34. The suture 26 may also extend through the sealing plug 18. The second lumen 36 may be used as a blood flashback lumen. A cross-sectional size of the second lumen 36 may be sized great enough for blood flow to occur.

Figure 4:
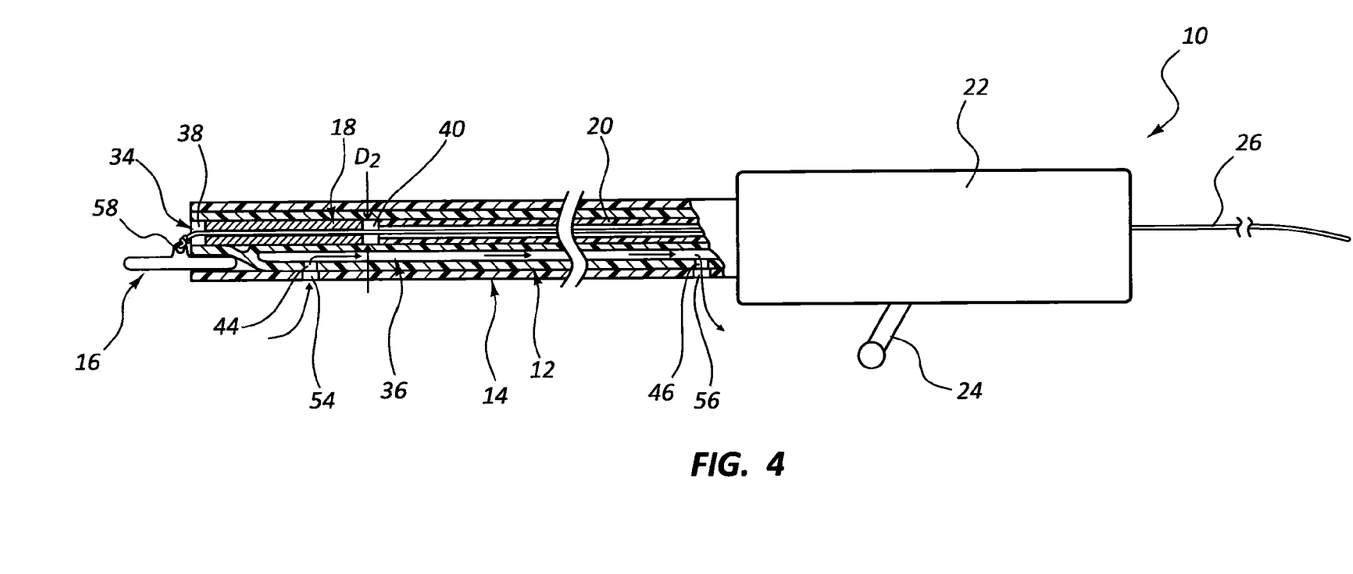
FIG. 4 is a partial cross-sectional view of the vascular closure device of FIG. 1A.

The first lumen 34 includes a distal portion 38 having a diameter $D_1$ (see FIG. 6), and a proximal portion 40 having a diameter $D_2$ (see FIG. 4). A recess 42 may be formed in the distal portion 38 to accommodate the anchor 16 in the stowed position (see FIG. 5). The recess 42 may automatically be removed upon moving the anchor 16 into the released position shown in FIG. 6. In other embodiments, the recess 42 may be maintained at the distal portion 38 of the first lumen 34 after the anchor 16 is removed from the stowed position.

The second lumen 36 may include a distal port 44 and a proximal port 46. The distal port 44 may be referred to as an inlet opening or inlet port for the second lumen 36. The proximal port 46 may be referred to as an outlet opening or outlet port of the second lumen 36. The distal port 44 may be spaced a distance $L_1$ from a distal end of a carrier tube. The distance $L_1$ may depend on, for example, an angle of insertion of the carrier tube 12 into the vessel, and other parameters. In at least some examples, the proximal port 46 is positioned adjacent to the handle 22. The proximal port 46 is typically positioned at a location spaced apart from the patient so that blood flow through the proximal port 46 is visible by the operator when locating the vessel interior.

The distal and proximal ports 44, 46 may be formed through a sidewall of the carrier tube 12. The distal and proximal ports 44, 46 may extend laterally from an outer surface of the carrier tube 12 through the sidewall and into the second lumen 36. The distal port 44 may be spaced proximal of a distal end of the second lumen 36. The proximal port 46 may be positioned distal of a proximal end of the second lumen 36.

Figures 1A, 1B, 2:
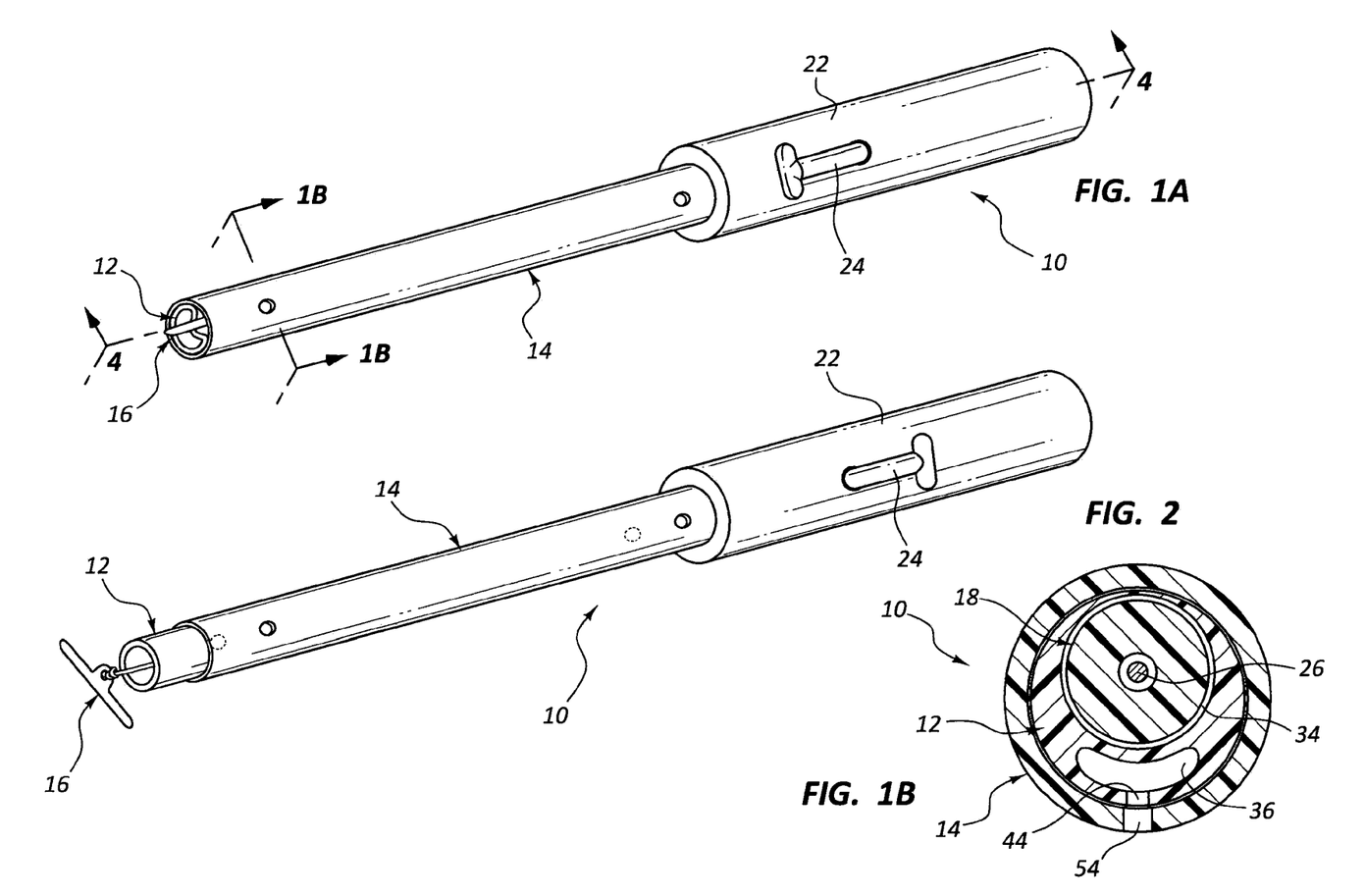
FIG. 1A is a perspective view of an example vascular closure device in accordance with the present disclosure.
FIG. 1B is a cross-sectional view of the vascular closure device of FIG. 1A taken along cross-section indicators 1B-1B.
FIG. 2 is a perspective view of the vascular closure device of FIG. 1A with a sleeve retracted to release an anchor.
Figure 3:
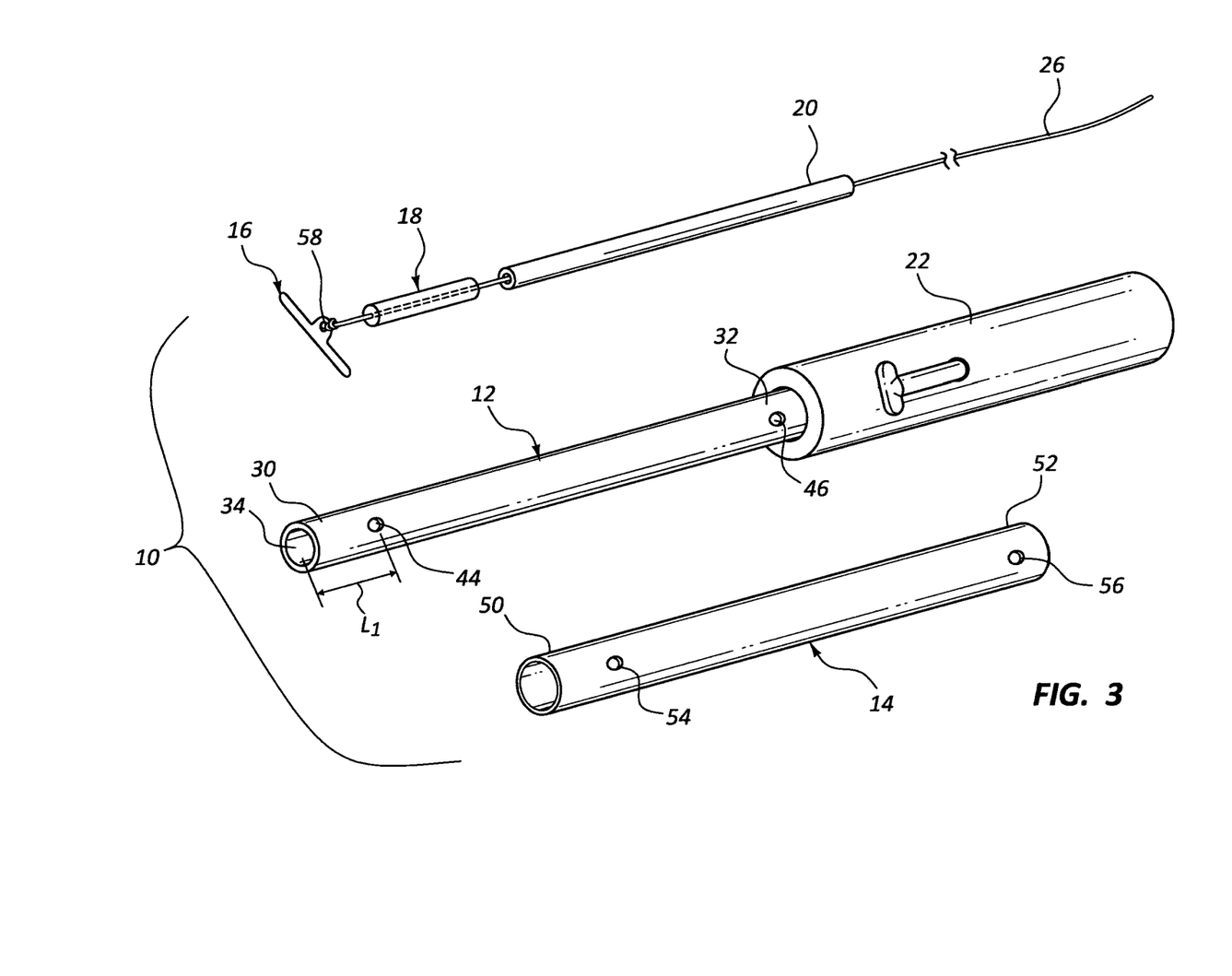
FIG. 3 is an exploded perspective view of the vascular closure device of FIG. 1A.

The first and second lumens 34, 36 may have different cross-sectional shapes as well as different cross-sectional sizes. At least FIG. 1B shows the first lumen 34 having a generally circular cross-sectional shape and the second lumen 36 having a crescent cross-sectional shape. Many other cross-sectional shapes are possible for each of the first and second lumens 34, 36 including, for example, an oval shaped first lumen 34 and a circular shaped second lumen 36. Typically, at least one of the first and second lumens 34, 36 has a low profile cross-sectional shape (e.g., a non-circular shape) that helps maintain a lower profile for the carrier tube 12 (e.g., a smaller peripheral size).

Figure 5:
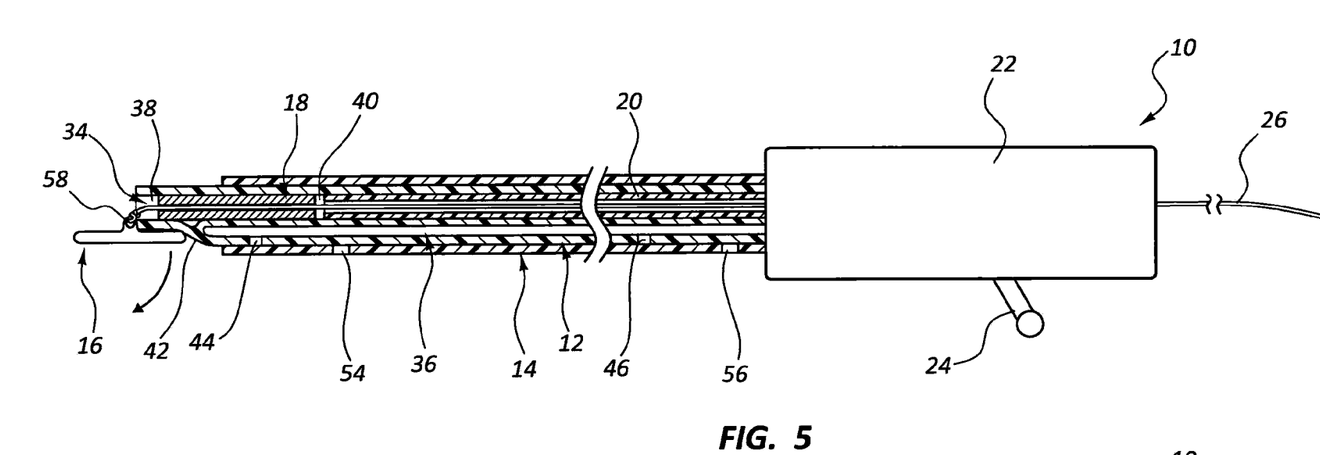
FIG. 5 is a partial cross-sectional view of the vascular closure device of FIG. 2 with the anchor in a stowed position.
Figure 6:
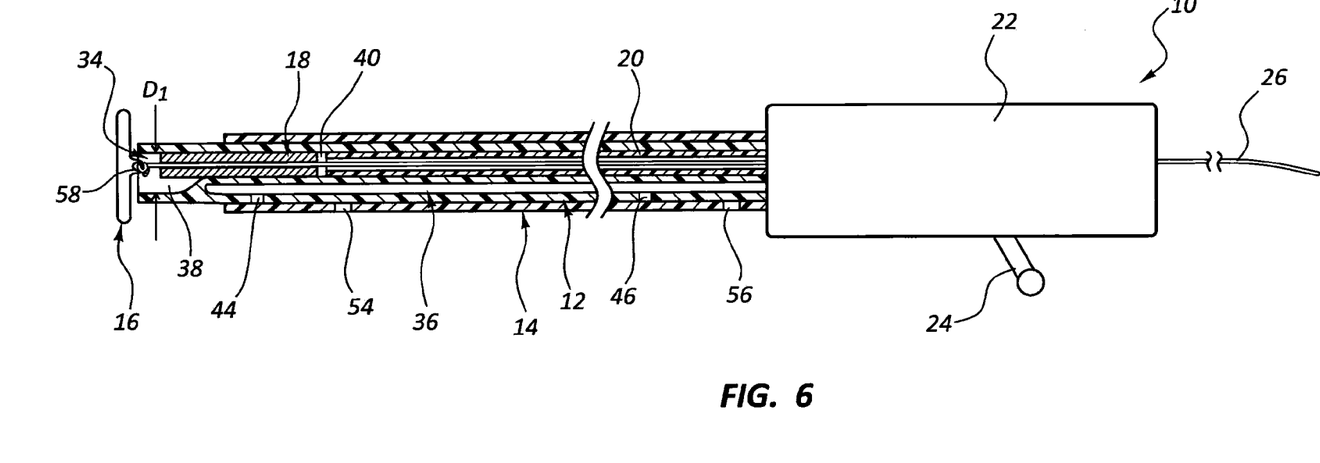
FIG. 6 is a partial cross-sectional view of the vascular closure device of FIG. 2 with the anchor in a released position.

The sealing plug 18 may be at least partially positioned within the distal portion 38 of the first lumen 34. In some arrangements (e.g., as shown in FIGS. 4-6) at least a portion of the sealing plug also extends into the proximal portion 40 of the first lumen 34. The sealing plug 18 may have different cross-sectional shapes and sizes that more closely match the diameters $D_1$, $D_2$ of the distal and proximal portions 38, 40 depending on the axial position of the sealing plug 18 within the first lumen 34.

The compaction tube 20 may also extend into the first lumen 34. A distal end of the compaction tube 20 may be positioned proximal of and adjacent to a proximal end of the sealing plug 18. The vascular closure device 10 may operate to advance the compaction tube 20 distally to compress and compact the sealing plug 18 to seal a vessel puncture as described in further detail below with reference to FIGS. 7-13. In some arrangements, the vascular closure device 10 may automatically advance the compaction tube 20 upon withdrawal of the handle 22 after disposing the anchor 16 within the vessel.

The actuator 24 may be carried by the handle 22. The actuator 24 may be operable between an advanced position (see FIGS. 1A and 4) and a retracted position (see FIGS. 2, 5 and 6). When in the advanced position, the distal and proximal ports 44, 46 are exposed to provide blood flow through the second lumen 36. When the actuator 24 is in the retracted position, at least one of the distal and proximal ports 44, 46 is inaccessible to restrict blood flow through the second lumen 36. In the example of FIGS. 1-6, the distal and proximal ports 44, 46 are both covered or inaccessible when the actuator 24 is in the retracted position.

The sleeve 14 includes distal and proximal ends 50, 52 and first and second ports 54, 56. The first and second ports 54, 56 may be referred to as secondary ports or sleeve ports. FIG. 1A shows the first and second ports 54, 56 aligned with the distal and proximal ports 44, 46 to provide fluid flow from outside of the sleeve 14 and into the second lumen 36. FIG. 1B and FIG. 4 show the alignment of first port 54 with the distal port 44 and the resultant flow path into the second lumen 36. A similar alignment may exist for the second port 56 with the proximal port 46 as shown in FIG. 4.

The sleeve 14 may be operated into a retracted or unaligned position in which at least one of the first and second ports 54, 56 is not aligned with the distal and proximal ports 44, 46, respectively. FIGS. 2, 5 and 6 show the sleeve 14 retracted so that neither of the first and second ports 54, 56 are aligned with the distal and proximal ports 44, 46, respectively. Other arrangements are possible in which the sleeve is moved in a different direction (e.g., rotated) to move the first and second ports 54, 56 out of alignment with the distal and proximal ports 44, 46. The sleeve 14 may be in a closed or covered position when at least one of the first and second ports 54, 56 are out of alignment with the distal and proximal ports 44, 46, respectively (e.g., in the position of FIGS. 2, 5 and 6).

The sleeve 14 may be used to retain the anchor 16 in a predetermined position relative to the carrier tube 12. FIGS. 1A and 4 show a portion of the anchor 16 positioned between an outer surface of the carrier tube 12 adjacent to the distal portion 38 of the first lumen 34 and an inner surface of the sleeve 14. This position of the anchor 16 may be referred to as a stowed or delivery position. The stowed position for the anchor 16 may be maintained while the vascular closure device 10 is inserted through a vessel puncture and the distal and proximal ports 44, 46 and second lumen 36 are used as a flashback feature to determine whether the anchor 16 is positioned within the vessel.

Once the position of the anchor 16 within the vessel is verified, the actuator 24 may be operated between the advanced position of FIG. 1A and the retracted position of FIG. 2 to move the sleeve 14 relative to the carrier tube 12. A comparison of FIGS. 4 and 5 shows how the sleeve 14 is moved from a first position storing the anchor 16 to a second position in which the anchor 16 is released to rotate relative to the carrier tube 12. When the anchor 16 is released, the anchor 16 may rotate into an operation position as shown in FIG. 6 in which the anchor 16 is able to contact an inner surface of the vessel adjacent to the puncture to perform an anchor function and a sealing function for the vascular closure device 10.

Operating the actuator 24 to retract the sleeve 14 relative to the carrier tube 12 may provide a dual function. A first function may be to move the first and second ports 54, 56 between a position aligned with the distal and proximal ports 44, 46, wherein blood flashback is possible, and a second position wherein the first and second ports 54, 56 are unaligned with the distal and proximal ports 44, 46 to stop blood flow through the second lumen 36. A second function may be to move the sleeve 14 from a first position in which the anchor 16 is held in a stowed position to a second position in which the anchor 16 is released to move into a position to perform anchoring and sealing.

The actuator 24 may be operated into an intermediate position between advanced and retracted positions. The intermediate position may provide blockage of the distal and proximal ports 44, 46 without releasing the anchor 16 from the stowed position. This intermediate position and related function may be helpful in at least some circumstances where it is not yet time to release the anchor but the operator wishes to stop blood flow through the blood flashback lumen. When the operator is ready to release the anchor, the actuator may be moved from the intermediate position to the retracted position shown in FIGS. 2, 5 and 6 so that the anchor 16 is released. In other arrangements, separate actuators may be used to control access to the distal and proximal ports 44, 46 and to control release of anchor 16.

Figure 7:
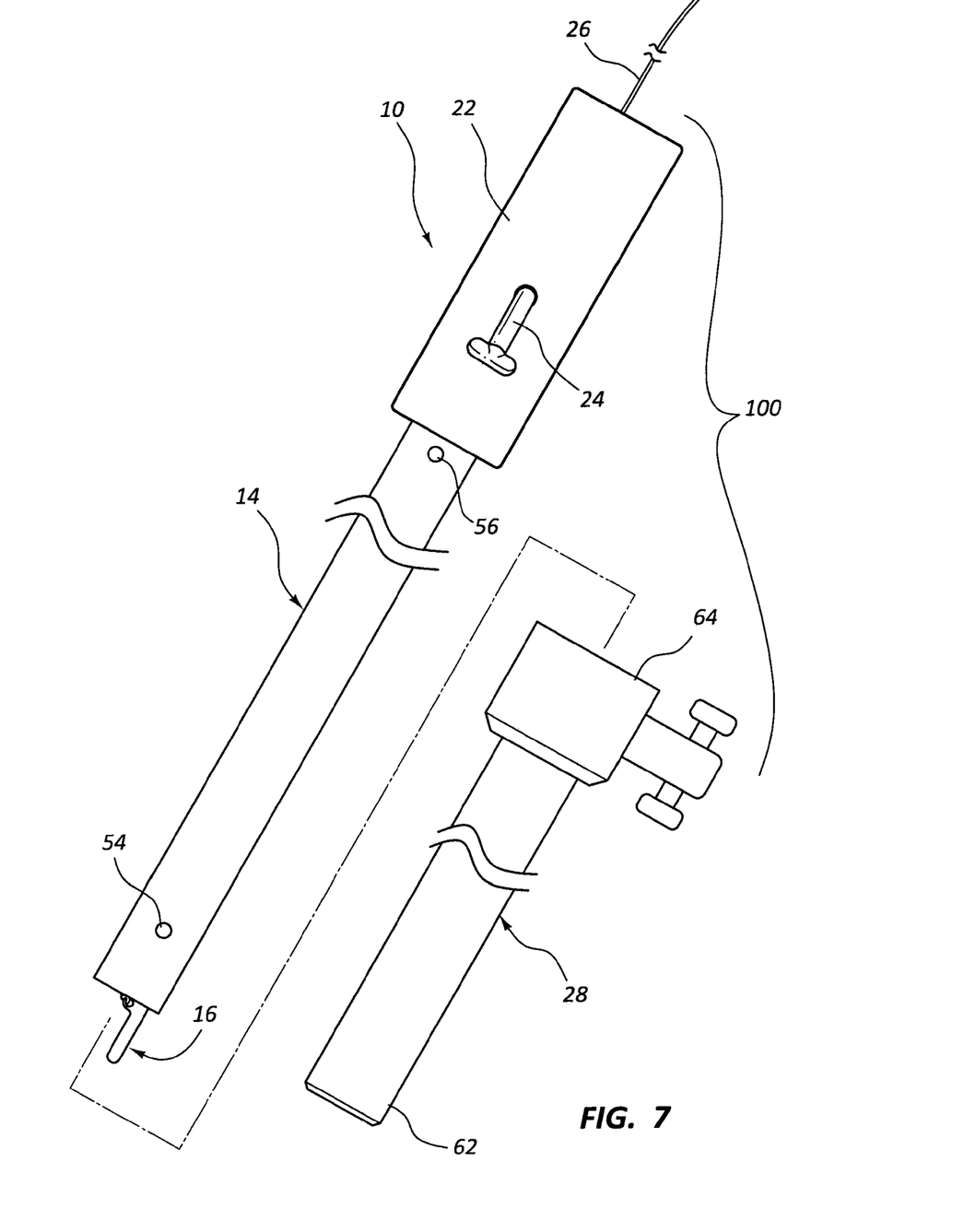
FIG. 7 is an exploded perspective view of an example vascular closure system including the vascular closure device of FIG. 1A.

Referring now to FIGS. 7-13, a method of treating a tissue puncture using the vascular closure device 10 is shown and described. The vascular closure device 10 may be part of a vascular closure system 100 as shown in FIG. 7. The vascular closure system 100 includes the vascular closure device 10 and an insertion sheath 28. The insertion sheath 28 includes a distal end 62 and a hub 64. The vascular closure device 10 is inserted through the hub 64 until a distal end of the vascular closure device 10 protrudes distally beyond the distal end 62 of the insertion sheath 28.

Figure 8:
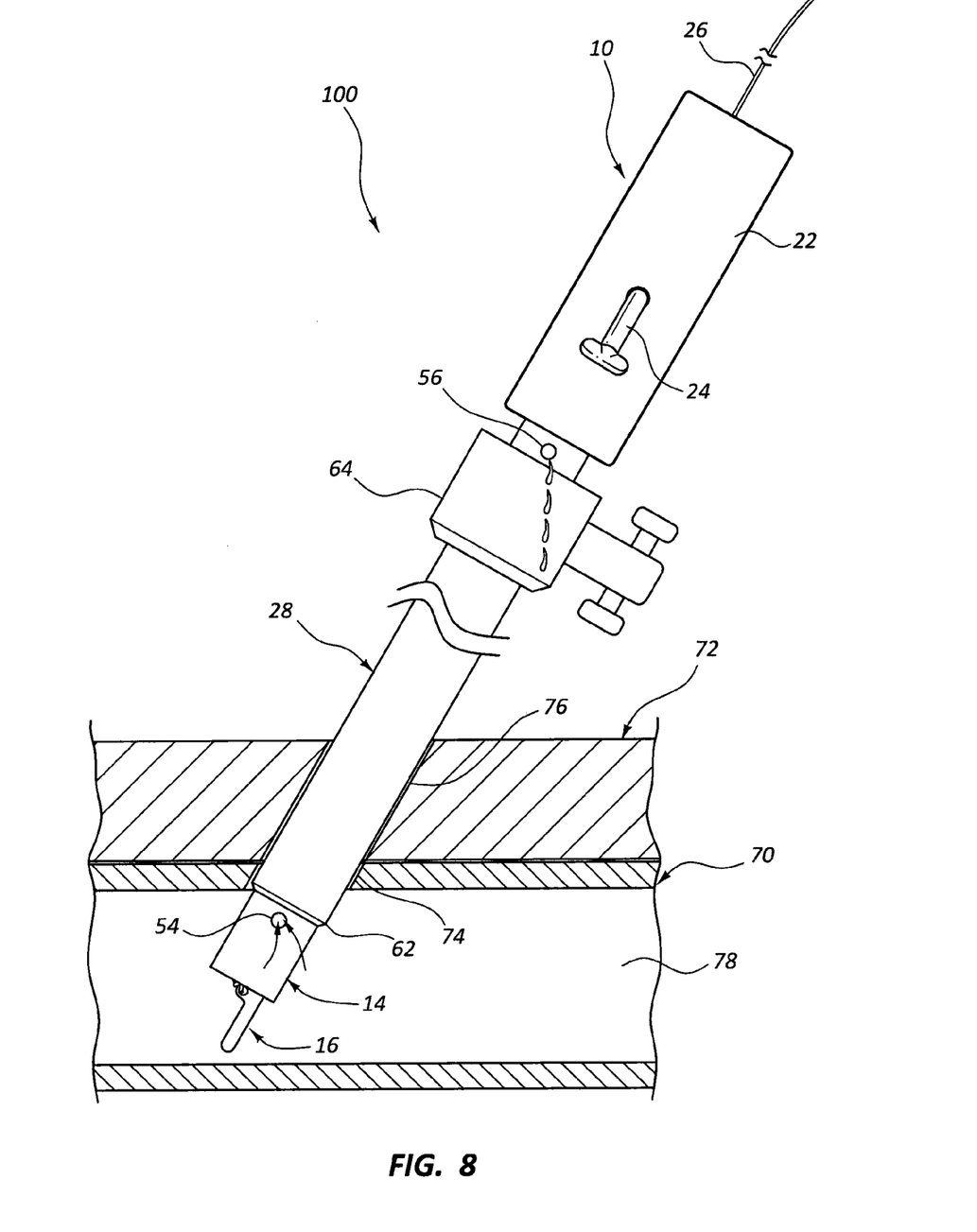
FIGS. 8-13 show the vascular closure system of FIG. 7 in use sealing a vessel puncture in accordance with the present disclosure.

Typically, the insertion sheath 28 is inserted through a percutaneous incision 76 of a tissue layer 72 and through a tissue puncture 74 into a vessel interior 78 of a vessel 70. The vascular closure device 10 is inserted through the insertion sheath 28 until a distal end portion of the vascular closure device 10 protrudes distally beyond the insertion sheath 28. The vascular closure device 10 may be arranged with the sleeve 14 in the aligned position such that when the first port 54 is exposed distally beyond the distal end 62 of the insertion sheath 28 blood is able to flow through the distal port 44 and into the second lumen 36 of the carrier tube 12. The blood flows through the second lumen 36 and out of the proximal port 46 and second port 56 as shown in FIG. 8. The operator receives a visual indication that the anchor 16 is positioned within the vessel interior 78 by the flow of blood out of the second port 56.

Figure 9:
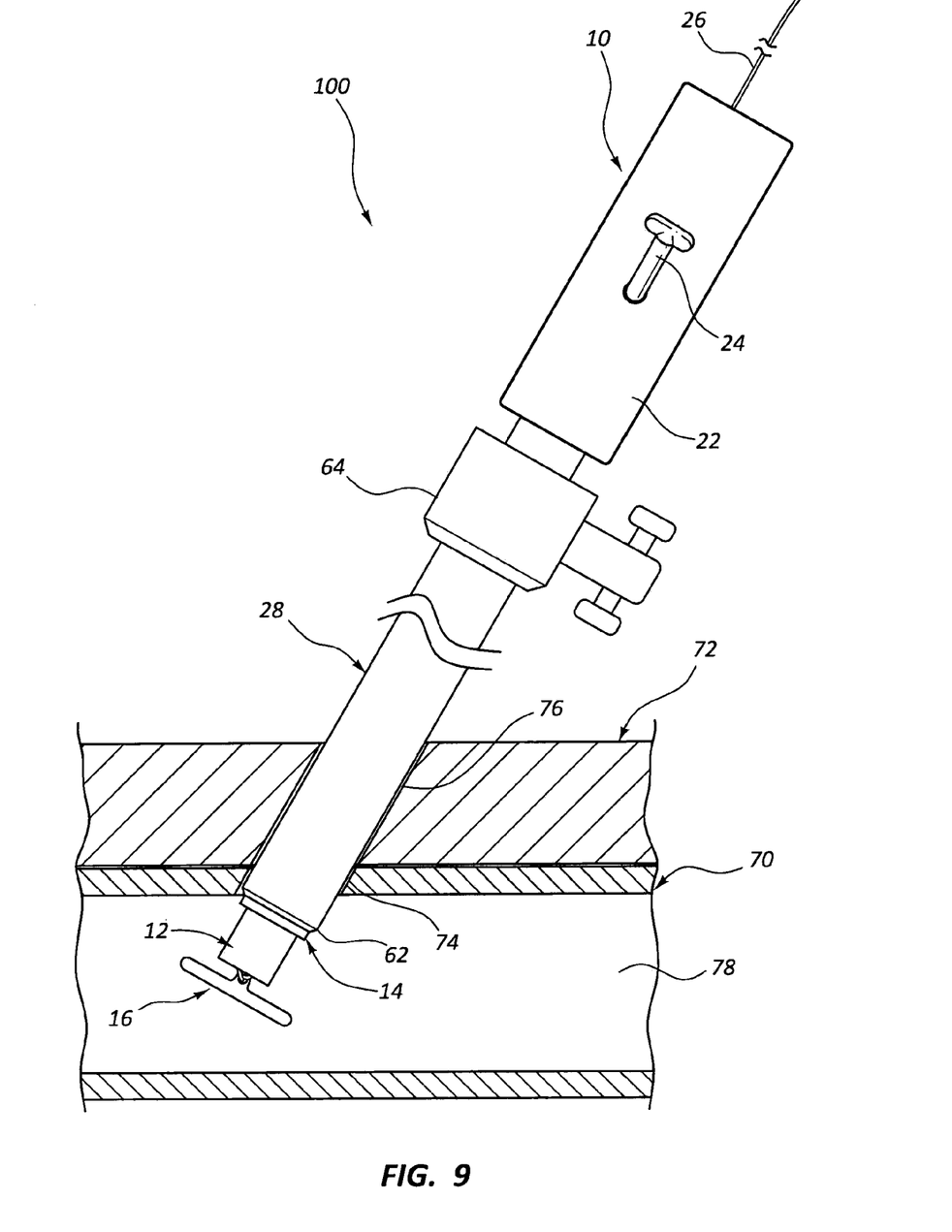
Figure 10:
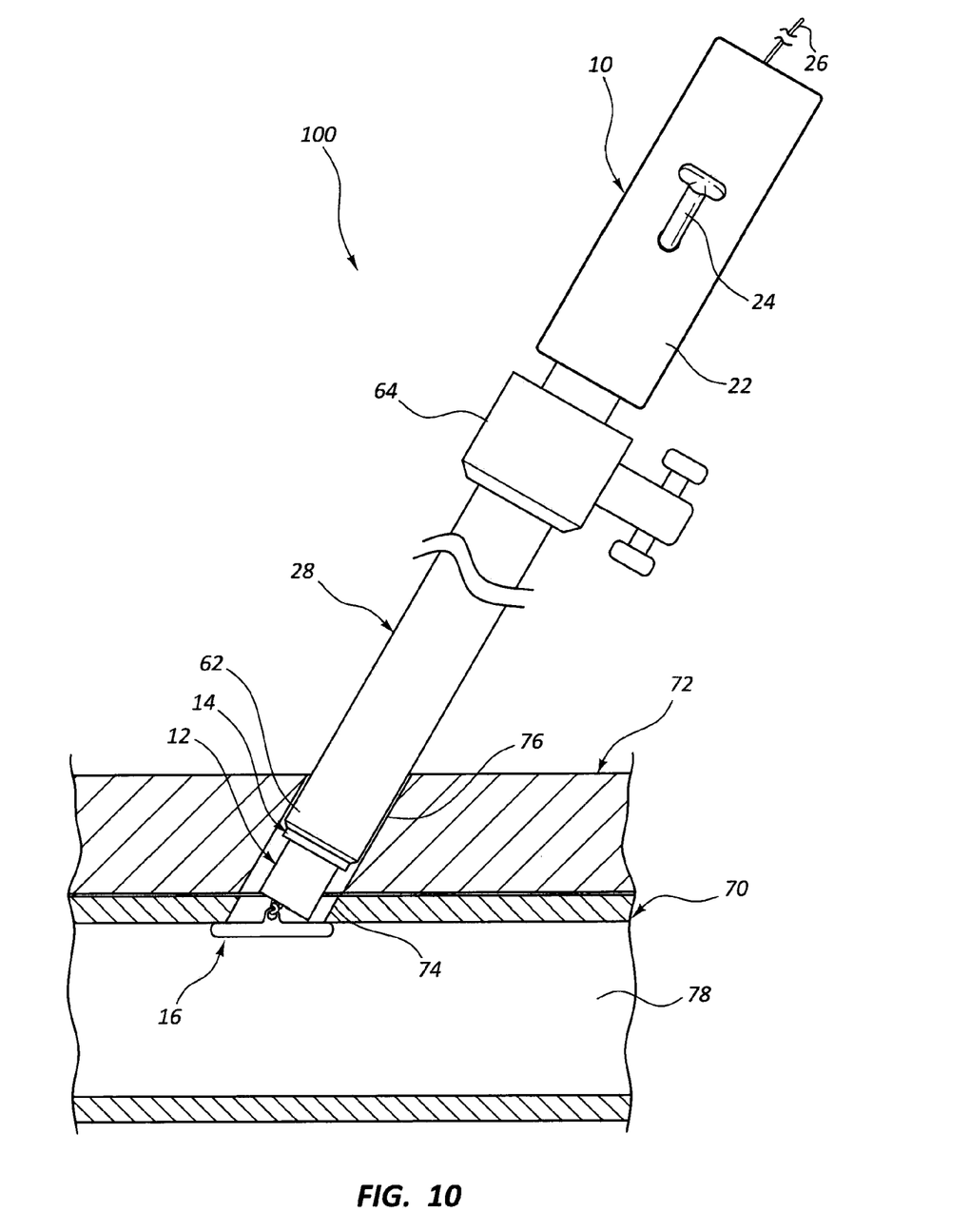
Figure 11:
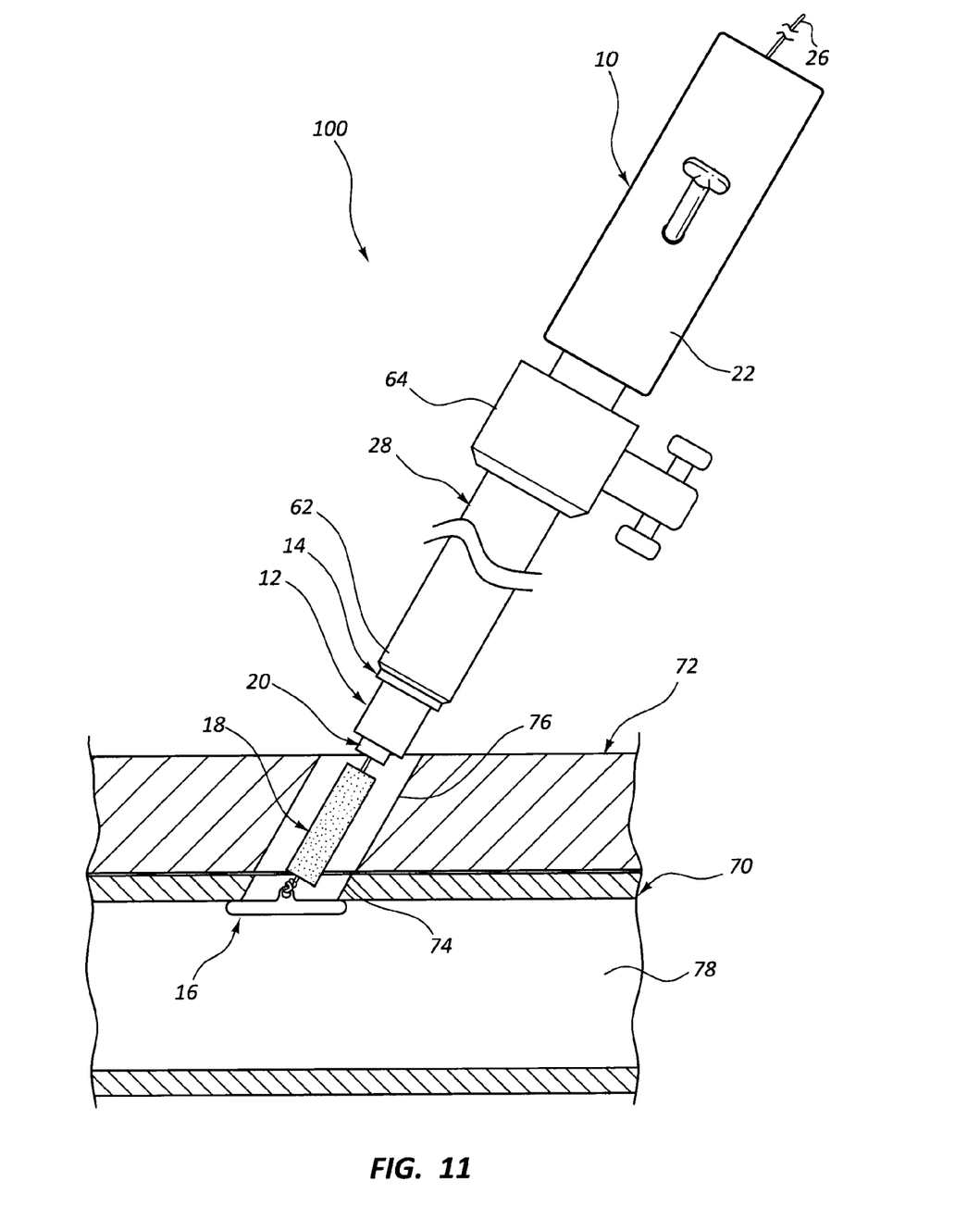
Figure 12:
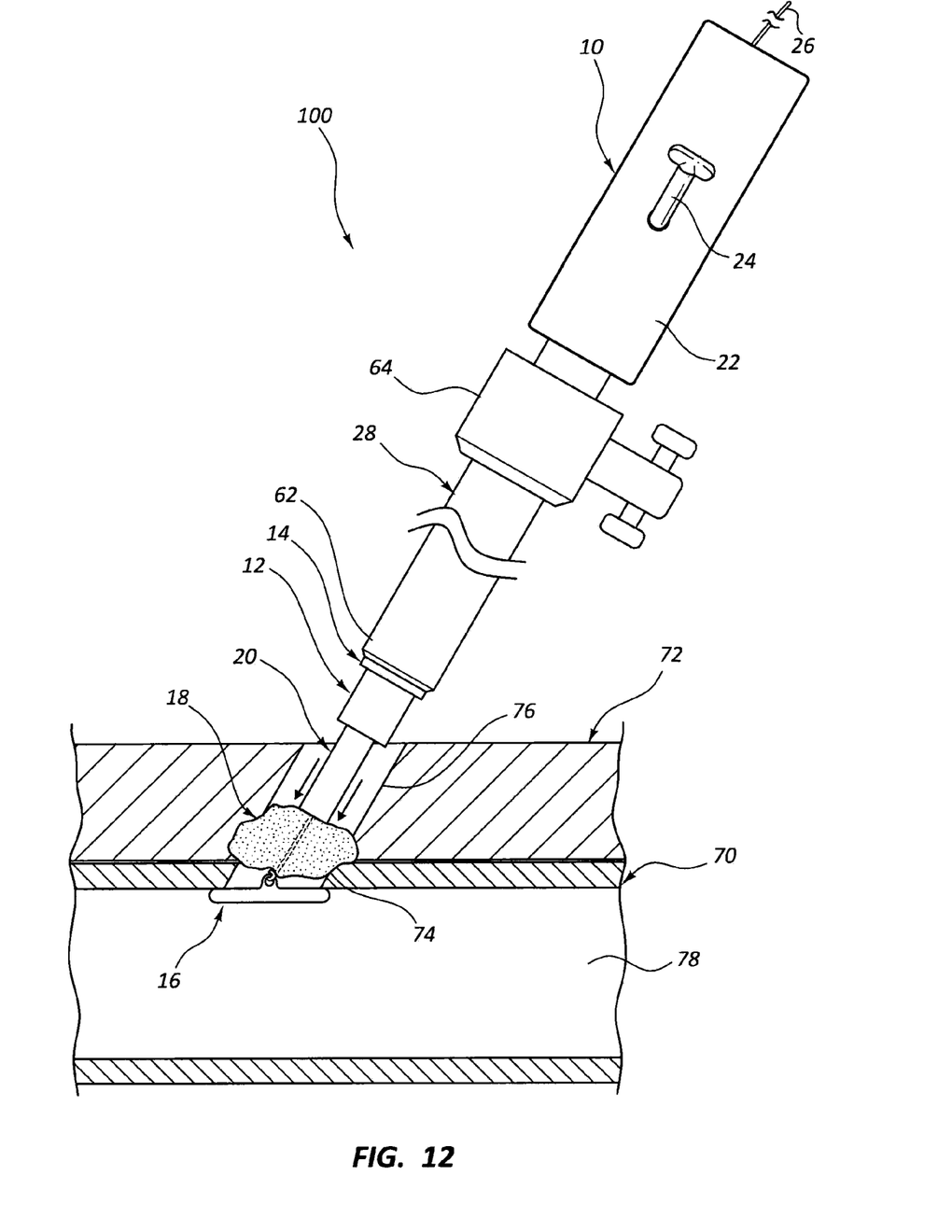

Referring now to FIG. 9, the actuator 24 is operated into a retracted position to retract the sleeve 14 relative to the carrier tube 12. This retraction shuts off blood flow through the second lumen 36. The retraction of sleeve 14 also releases the anchor 16 into an operating position as shown in FIG. 9.

The operator then retracts the vascular closure system 100 until the anchor 16 contacts an inner surface of vessel 70 adjacent to the tissue puncture 74. Positioning the anchor 16 in this manner may at least partially occlude blood flow through the tissue puncture 74 while concurrently anchoring the vascular closure device 10 within the tissue tract 76.

The operator then deposits the sealing plug 18 within the percutaneous incision 76. The sealing plug 18 may be deposited, for example, by retracting the carrier tube 12 (and sleeve 14) and insertion sheath 28 while maintaining an axial position of the sealing plug 18. An axial position of the compaction tube 20 may be maintained to help hold the sealing plug 18 in a fixed axial position while retracting the carrier tube 12 and insertion sheath 28.

Figure 13:
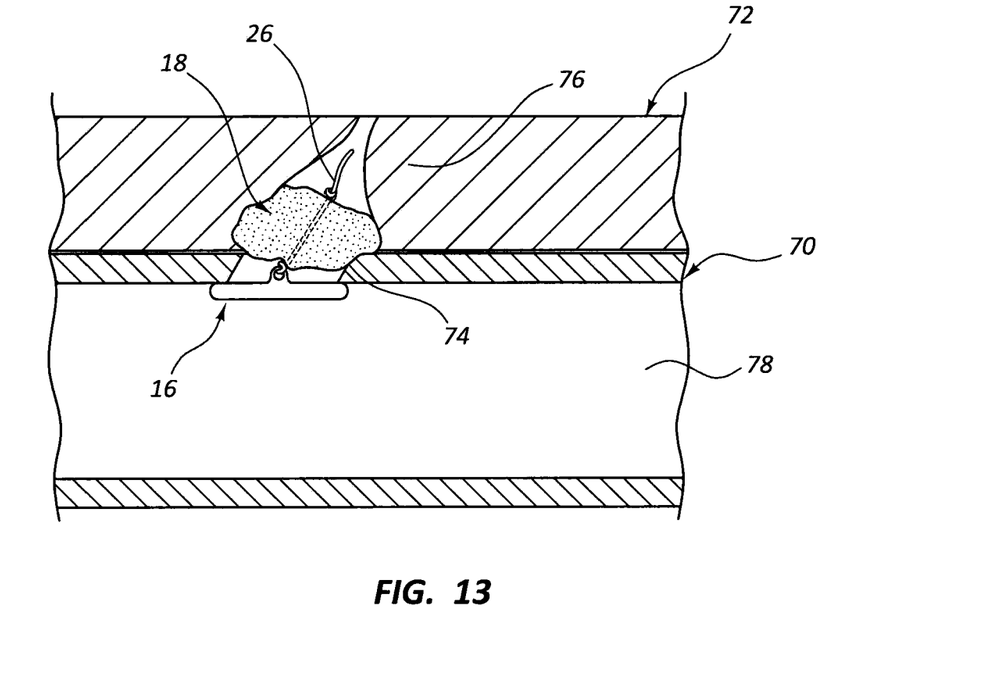

The compaction tube 20 is then advanced to compact or compress the sealing plug 18 toward the anchor 16. The sealing plug 18 may fill at least portions of the tissue puncture 74 and percutaneous incision 76 to provide a seal that limits blood flow through tissue puncture 74 and percutaneous incision 76. A knot may be advanced along suture 26 to maintain a positive connection between the sealing plug 18 and anchor 16. The knot may also maintain tension in the suture 26 that holds the sealing plug 18 in a compressed or compacted position against the anchor 16. The suture 26 may then be cut off (e.g., within the percutaneous incision 76) to release the remaining portions of the vascular closure system 100 from the anchor 16 and sealing plug 18 as shown in FIG. 13.

Many other configurations are possible to provide at least some of the same or similar functions as described above with reference to vascular closure system 100. For example, the sleeve 14 may be used to control access to the distal and proximal ports 44, 46 while a separate structure may be used to maintain the anchor 16 in the stowed position and then later release the anchor 16. In other embodiments, the anchor may include an expandable member that is expandable after being positioned within the vessel rather than being a fixed size structure such as the anchor 16 that requires movement (e.g., rotation) into an operating position after being positioning in the vessel. The expandable anchor may be stowed without using a sleeve or other size restricting structure.

Figures 14, 15:
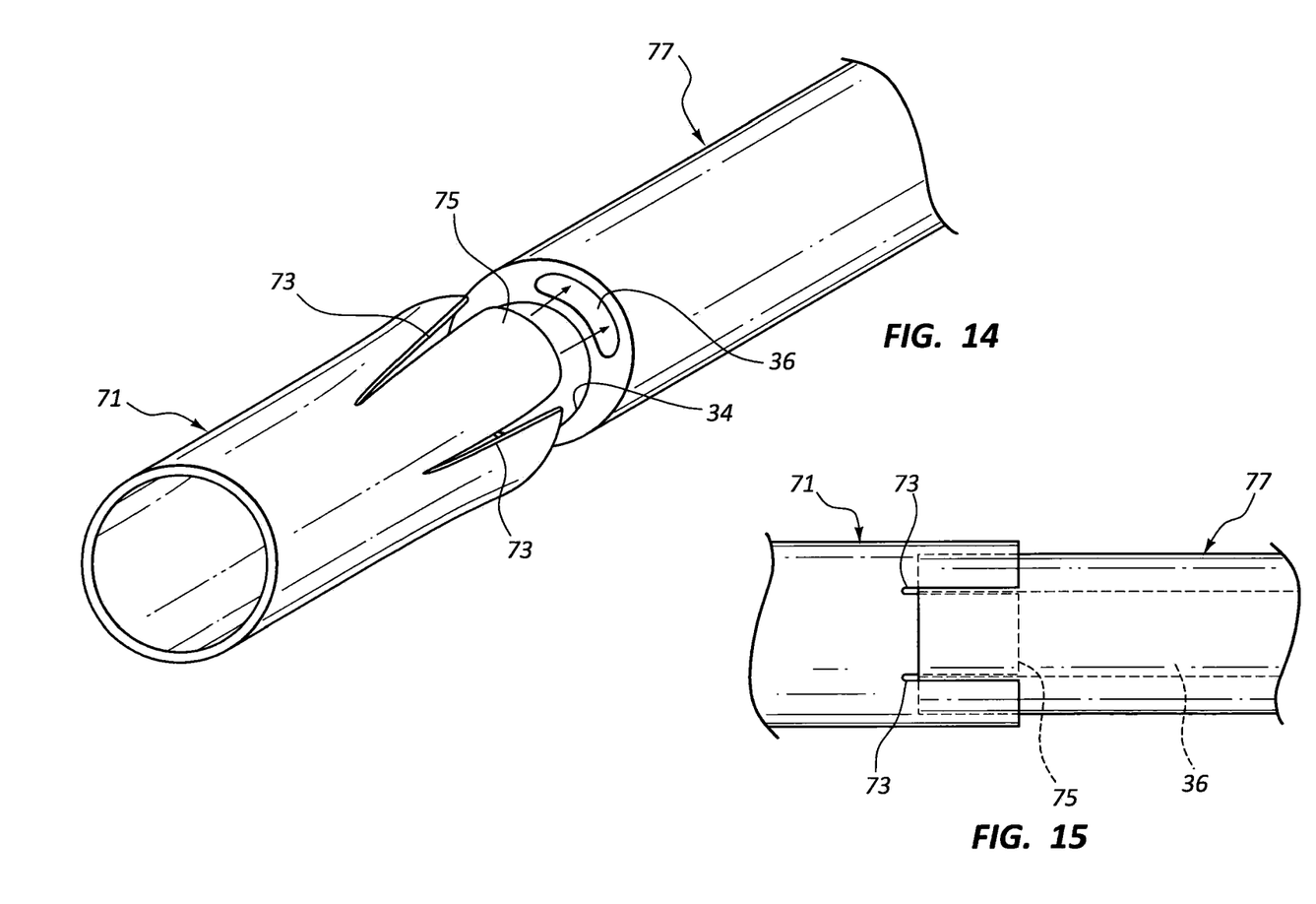
FIG. 14 is an exploded perspective view of a distal end portion of a carrier tube of the vascular closure device of FIG. 1A as part of manufacturing the carrier tube.
FIG. 15 is a top view of the carrier tube of FIG. 14 assembled together as part of manufacturing the carrier tube.

The structure of the carrier tube 12 may be formed in a variety of ways. FIGS. 14 and 15 show one way in which the distal end portion of the carrier tube 12 is formed such that the second lumen 36 terminates at a location spaced proximal of a distal end surface of the carrier tube 12. A distal tip portion 71 has a pair of slits 73 formed therein and a proximal portion 77 includes first and second lumens 34, 36. A tab 75 formed by the slit 73 is inserted into the second lumen 36 to fill the distal portion of the second lumen 36, as shown in FIG. 15. The overlapping portion of the distal tip 71 and proximal portion 77 may then be treated to secure the distal tip 71 to the proximal portion 77. In one example, a hot jaw, laser weld, or other method of applying heat may be used to provide an integral bonding of the materials of the distal tip 71 with the proximal portion 77. In other examples, adhesives or other bonding techniques may be used to connect the distal tip 71 to the proximal portion 77.

One advantage related to the carrier tube 12 described herein is that it eliminates the need for a sheath exchange that is often required when treating a vessel puncture. Typically, blood flashback features are provided in the insertion sheath. An insertion sheath having blood flashback capability must be exchanged with a sheath that is typically already in position in the vessel as part of performing a medical procedure on the patient. After the sheath exchange, a vascular closure device is advanced through the insertion sheath having the blood flashback capability. By providing the blood flashback features within the carrier tube of the vascular closure device, the sheath exchange may be eliminated by eliminating the need for a sheath with flashback capability.

One advantage to using the sleeve 14 disclosed herein may be to help control flow through the blood flashback lumen when the blood flashback features of the carrier tube are not needed. The sleeve may also be used to help hold the anchor in a stowed position while advancing the vascular closure device through the insertion sheath and into the vessel interior. As discussed above, embodiments are possible in which the same advantages related to flashback capability are possible without using a sleeve.

The general structure and function of vascular closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engageable" are also used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A vascular closure device, comprising:
a carrier tube having at least first and second lumens, the first lumen holding a sealing member, the second lumen being configured to provide blood flow from a distal opening thereof to a proximal opening thereof;
an anchor positioned at the distal end of the carrier tube;
a sleeve positioned on the carrier tube and movable from a first position wherein blood flow through the second lumen is unobstructed, and a second position covering the distal and proximal openings to block blood flow through the second lumen;
wherein the proximal and distal openings are formed in a sidewall of the carrier tube;
wherein the sleeve includes at least first and second openings formed in a sidewall thereof, and the first and second openings of the sleeve are aligned with the proximal and distal openings of the second lumen when the sleeve is in the first position.

2. The vascular closure device of claim 1, wherein the anchor is positionable between an outer surface of the carrier tube and an inner surface of the sleeve when the sleeve is in the first position, and moving the sleeve from the first position to the second position releases the anchor to rotate relative to the carrier tube.

3. The vascular closure device of claim 2, wherein a distal end portion of the carrier tube is elastically deformable to define a recess along an outer surface thereof, a portion of the anchor being positioned in the recess.

4. The vascular closure device of claim 1, wherein the second lumen terminates at a location along the carrier tube proximal of the first lumen.

5. The vascular closure device of claim 1, wherein the sleeve moves axially between the first and second positions.

6. The vascular closure device of claim 1, wherein the first lumen includes a distal portion and a proximal portion, the distal portion having a greater cross-sectional size than the proximal portion.

7. The vascular closure device of claim 1, further comprising a handle assembly connected to a proximal end of the carrier tube and a proximal end of the sleeve, the handle assembly comprising an actuator operable to move the sleeve relative to the carrier tube.

8. The vascular closure device of claim 1, wherein the second lumen has a non-circular cross sectional shape.

9. A vascular closure system, comprising:
an insertion sheath having a distal end and being configured for insertion through a vessel puncture;
a vascular closure device including:
a carrier tube having first and second lumens, the carrier tube being positionable within the insertion sheath;
an anchor positioned at a distal end of the carrier tube;
a sleeve positionable over the carrier tube;

a sealing plug positioned in the first lumen of the carrier tube and coupled to the anchor with a suture that extends through the first lumen;

wherein the second lumen comprises inlet and outlet ports configured to provide blood flow into and out of the second lumen;

wherein the sleeve is movable relative to the carrier tube from a first position, holding the anchor in a stored position and permitting blood flow through the second lumen, to a second position where the anchor is in a released position and blood flow through the second lumen is blocked; and wherein the sleeve includes at least a first port formed in a sidewall thereof that aligns with the outlet port of the carrier tube when the sleeve is in the first position.

10. The vascular closure system of claim 9, wherein the first lumen has at least one of a variable cross-sectional shape and a variable cross-sectional size along a length thereof.

11. The vascular closure system of claim 9, wherein the second lumen terminates at a location spaced proximal of a distal end of the carrier tube.

12. The vascular closure system of claim 9, wherein the sleeve is movable from the second position to the first position to move the anchor from the released position to the stored position.

13. A method of operating a vascular closure device, comprising:

providing a carrier tube having first and second lumens, a sleeve positionable over the carrier tube, an anchor positioned at a distal end of the carrier tube, and a sealing plug positioned in the first lumen of the carrier tube and coupled to the anchor with a suture that extends through the first lumen;

moving the sleeve relative to the carrier tube from a first position holding the anchor in a stored position and permitting blood flow through the second lumen, to a second position wherein the anchor is in a released position and blood flow through the second lumen is blocked;

wherein the carrier tube includes at least one distal port formed in a sidewall thereof, the sleeve providing access to the at least one distal port when in the first position and covering the at least one distal port in the second position;

wherein the sleeve includes at least one opening formed in a sidewall thereof that aligns with the at least one distal port when the sleeve is in the first position.

14. The method of claim 13, wherein the anchor is positioned between an outer surface of the carrier tube and an inner surface of the sleeve when in the stored position, and the anchor is pivotable relative to the carrier tube when in the released position.

15. A method of treating a puncture in a vessel, comprising:

providing an insertion sheath and a vascular closure device, the vascular closure device comprising a carrier tube having at least first and second lumens, a sleeve positionable over the carrier tube, an anchor positioned at a distal end of the carrier tube, and a sealing plug positioned in the first lumen of the carrier tube and coupled to the anchor with a suture that extends through the first lumen;

inserting the insertion sheath into the puncture;

arranging the sleeve relative to the carrier tube in a first position in which the anchor is held in a stored position and a fluid path through the second lumen is open;

inserting the vascular closure device through the insertion sheath until blood flows through the second lumen;

moving the sleeve from the first position into a second position to release the anchor and close the fluid path;

wherein the carrier tube includes a distal port formed in a sidewall thereof providing access to the second lumen, and the carrier tube covers the distal port when in the second position;

withdrawing the vascular closure device to draw the anchor into contact with an inner surface of the vessel adjacent to the puncture and to deposit the sealing plug adjacent to the puncture exterior of the vessel to seal the puncture.

16. The method of claim 15, wherein the vascular closure device further includes a compaction member, the method comprising operating the compaction member to compact the sealing plug toward the anchor.

17. The method of claim 15, wherein moving the sleeve includes retracting the sleeve in a proximal direction.

* * * * *